(12) United States Patent
Tweardy

(10) Patent No.: US 7,549,970 B2
(45) Date of Patent: Jun. 23, 2009

(54) CERVICAL BRACE

(75) Inventor: Lisa A. G. Tweardy, Moorestown, NJ (US)

(73) Assignee: Ossur HF (IS)

( * ) Notice: Subject to any disclaimer, the term of this patent is extended or adjusted under 35 U.S.C. 154(b) by 0 days.

(21) Appl. No.: 11/077,675

(22) Filed: Mar. 11, 2005

(65) Prior Publication Data

US 2005/0159692 A1    Jul. 21, 2005

Related U.S. Application Data

(62) Division of application No. 10/001,451, filed on Oct. 23, 2001, now Pat. No. 6,921,376.

(51) Int. Cl.
*A61F 5/00* (2006.01)
*A61F 5/37* (2006.01)
*A61B 19/00* (2006.01)

(52) U.S. Cl. .............................. 602/18; 602/17; 602/19; 128/869; 128/876; 128/874; 128/DIG. 23

(58) Field of Classification Search .................... 602/17, 602/18, 19; 128/869, 873, 874, DIG. 23, 128/DIG. 15, DIG. 19
See application file for complete search history.

(56) References Cited

U.S. PATENT DOCUMENTS

| | | | |
|---|---|---|---|
| 2,820,455 A | 1/1958 | Hall | 602/18 |
| 2,904,040 A | 9/1959 | Hale | 602/18 |
| 4,502,471 A | 3/1985 | Owens | |
| 4,515,153 A * | 5/1985 | Calabrese | 602/18 |
| 4,582,051 A * | 4/1986 | Greene et al. | 602/18 |
| 4,628,913 A * | 12/1986 | Lerman | 602/18 |
| 4,677,969 A * | 7/1987 | Calabrese | 602/18 |
| 4,807,605 A * | 2/1989 | Mattingly | 602/19 |
| 4,913,135 A | 4/1990 | Mattingly | 602/18 |
| 5,201,702 A | 4/1993 | Mars | 602/17 |
| 5,531,669 A | 7/1996 | Varnau | |
| 5,575,763 A | 11/1996 | Nagata et al. | |
| 5,624,387 A | 4/1997 | McGuinness | |
| 5,637,067 A | 6/1997 | Ausmus | |
| 5,776,088 A | 7/1998 | Sereboff | |
| 5,964,722 A | 10/1999 | Goralnik et al. | |
| 6,045,522 A | 4/2000 | Grober | |
| 6,213,765 B1 | 4/2001 | Standerwick et al. | |
| 6,267,741 B1 | 7/2001 | Lerman | 128/DIG. 23 |
| 6,315,746 B1 * | 11/2001 | Garth et al. | 602/18 |
| 6,770,047 B2 * | 8/2004 | Bonutti | 602/18 |

* cited by examiner

*Primary Examiner*—Patricia Bianco
*Assistant Examiner*—Tarla Patel
(74) *Attorney, Agent, or Firm*—Schnader Harrison Segal & Lewis LLP

(57) ABSTRACT

A cervical brace having a cervical collar. The collar has a front collar portion and a rear collar potion wherein the rear collar portion comprises an occipital support. A vest comprising a front vest portion and a back vest portion is attached to the front collar portion to limit movement of the front vest portion with respect to the cervical collar while the back vest portion is free to move with respect to the cervical collar rear portion.

20 Claims, 10 Drawing Sheets

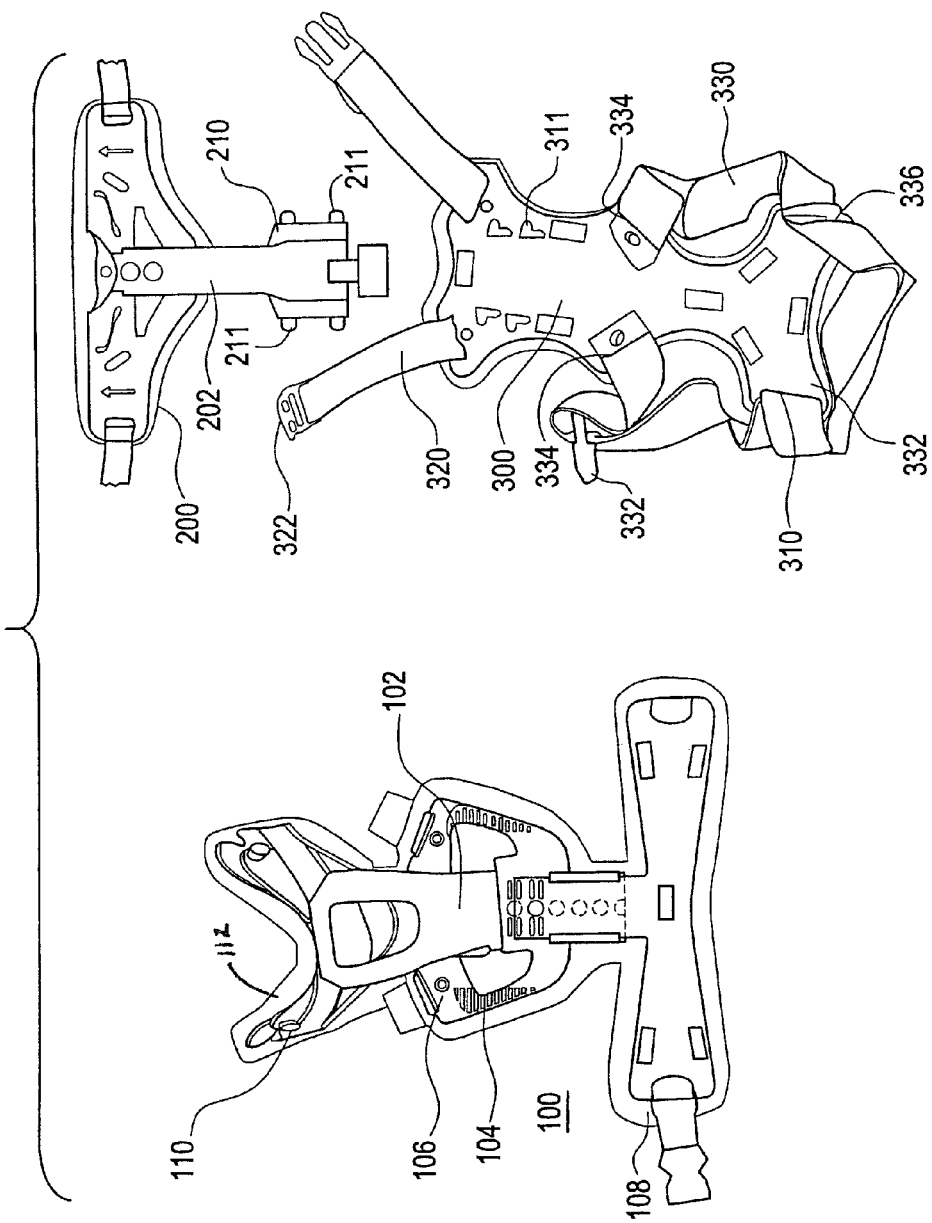

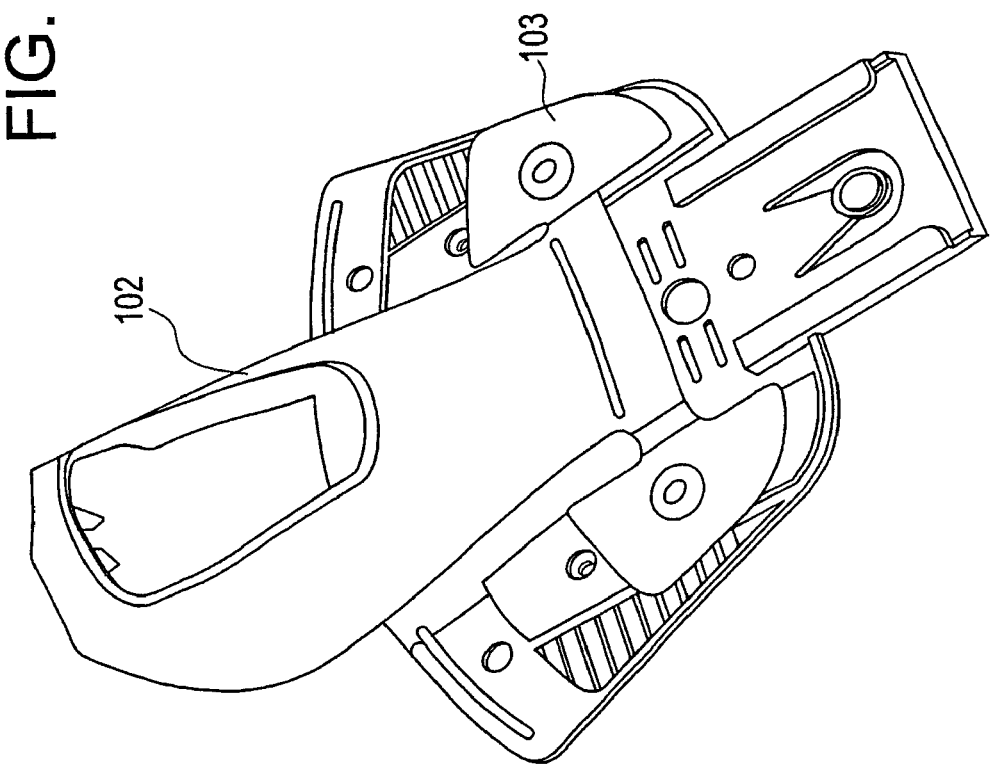

US 7,549,970 B2

CERVICAL BRACE

This application is a division of, and claims priority to, application Ser. No. 10/001,451 having a filing date of Oct. 23, 2001.

TECHNICAL FIELD

The present invention relates, in general, to orthopedic units and, in particular, to cervical collars and/or braces.

BACKGROUND OF THE INVENTION

Various cervical thoracic orthoses have been developed for treating cervico-thoracic injuries of the upper thoracic spine and lower cervical spine. Some of these are collars which function to partially immobilize the head and neck of the patient and relieve spasm or strain by transferring load or force from the head of a patient to the shoulders or adjacent areas of the patient. Other devices designed for complete or near complete immobilization of the head and neck of the patient have also been developed.

A feature, preferably included in cervical thoracic orthoses to overcome limited adaptability or to accommodate the body of the patient and the particular ailment prompting the need for wearing an orthosis, is the facility for adjusting the relative positions of various components of the cervical thoracic orthosis. Currently available orthoses generally lack such features.

Various types of cervical thoracic orthoses have been developed in treating conditions of the cervical spine, cervico-thoracic junction (i.e. the upper thoracic spine and lower cervical spine) or occipital-cervical junction (i.e. occiput to upper cervical spine). Some of these are collars, which are used merely where support for the head and neck is needed. The primary objective for the use of such a collar is to partially immobilize the head and neck, to maintain a desired spinal alignment, to provide support for the head, and to relieve any spasm or strain to which the neck muscles may be subjected by transmitting load or force from the head to the shoulders or adjacent area. Other collars are intended for use where near complete immobilization of the head and neck are necessary such as when a patient is attended to by emergency medical personnel prior to admission to a hospital. There are a multitude of cervical collars intended to perform one or more of the above-mentioned functions.

U.S. Pat. No. 5,776,088—Sereboff describes an adjustable, flexible cervical collar designed for universal use by providing vertically adjustable movable sections that support the chin and the back of the head, which can also be displaced around the circumference of the collar.

Other collars intended for partial or total immobilization are shown in U.S. Pat. No. 4,502,471—Owens and U.S. Pat. No. 4,582,051—Greene et al. Both these collars attempt to provide stability by providing a front and rear brace that connects a collar to a lower section that either rests on the patients shoulders or is a belt surrounding the thorax. A more elaborate version of such a brace is disclosed by U.S. Pat. No. 5,531,669—Varnau, which has adjustable pads to support the chin and the occiput, that are in turn supported by flexible and vertically adjustable members that are attached to a vest that is fitted over the shoulders and which has a strap that surrounds the thorax.

Other prior art devices include cervical orthosis or a brace that restrains the head from movement by a band attached to the forehead of the patient, which is then restrained by connecting the band to the shoulders or upper thorax. Such a device is shown in U.S. Pat. No. 5,624,387—McGuiness, which uses a set of adjustable rods and bars to effect stabilization. Another device in this category is shown in U.S. Pat. No. 5,575,763—Nagata et al., which discloses restraint and stabilization using an integrally molded device that can only be fitted within narrow ranges of adjustment.

The highly constraining systems described above can cause unwanted compensatory movement of the spine as a result of mechanically overconstraining the brace. Device-induced compensatory motion can create additional orthopedic problems.

Thus there remains a long-felt, yet unmet, need for a cervico-thoracic orthosis that is comfortable to the wearer, allows better protection of the cervical junctions and can be easily adapted to a wide variety of patient phenotypes that exist, without the need for extensive customization.

SUMMARY OF THE INVENTION

Embodiments of the invention provide a cervical brace that includes a cervical collar and a vest assembly. The collar has a front collar portion and a rear collar portion wherein the rear collar portion comprises an occipital support. The vest has a front vest portion and a back vest portion and is attached to the front collar portion to limit movement of the front vest portion with respect to the cervical collar, while the back vest portion is free to move with respect to the cervical collar rear portion. The novel configuration may provide a more comfortable means of support and may allow increased stabilization. Additional embodiments provide adjustability for adaptation of the brace to a variety of patient phenotypes, without the need for extensive customization Methods of supporting the cervical spine of an injured patient are also disclosed, wherein a cervical collar, having a front collar portion and a rear collar portion with an occipital support is attached to a patient. A vest is attached to the patient wherein the vest has a front vest portion and a back vest portion. The front vest portion is attached to the front collar portion and the back vest portion is left free from attachment to the rear collar portion, to reduce or eliminate compensatory motion.

BRIEF DESCRIPTION OF THE DRAWINGS

FIG. 1A depicts sub-assemblies that together make up an illustrative embodiment of the cervical brace of the present invention.

FIG. 2 is an illustrative embodiment of the anterior sub-assembly shown in FIG. 1A and further illustrating the components thereof.

FIG. 6A is an illustrative view of a section of the anterior assembly of FIG. 6 taken through section 6A-6A.

DETAILED DESCRIPTION OF THE PREFERRED EMBODIMENTS

Embodiments of the present invention provide a cervical brace having a cervical collar and a freely moving back portion. The cervical collar is not rigidly connected to the back portion so the desired alignment of the spine is better maintained. The freely moving back portion reduces or eliminates compensatory motion, unlike conventional over-constrained systems. In an over-constrained cervico-thoracic bracing system unwanted motion at the cervical junctions occurs as a result of forces applied through the brace. This compensatory motion of the spine is seen during certain activities, such as transitioning from a sitting position to a standing position, or a prone position to a sitting position. There is less constraint on the system when the back is free to move from the collar allowing better stabilization of the cervical junctions. Conventional braces maintain relative position of the brace components. Therefore, as a patient moves from supine to standing or sitting, undesirable or compensatory forces may be imposed upon the neck and back causing the spine to move in an undesirable fashion. A patient using embodiments of the present invention may lay flat on their back with the head in the same relative position as when upright, which is the normal tendency. Conventional braces induce different relative position of the neck and back, whether prone, standing or sitting. As this is not natural, it can be very uncomfortable, and sometimes harmful to the patient. Use of a freely moving back portion for a cervical brace is not intuitive, as it is generally believed in the art that patients benefit from a maximum amount of constraint.

Although illustrative embodiments of the invention include a freely moving back portion, it is noted that the embodiments may include or accommodate a rear strut that can be attached to the rear portion if the need arises.

Figure 1B:
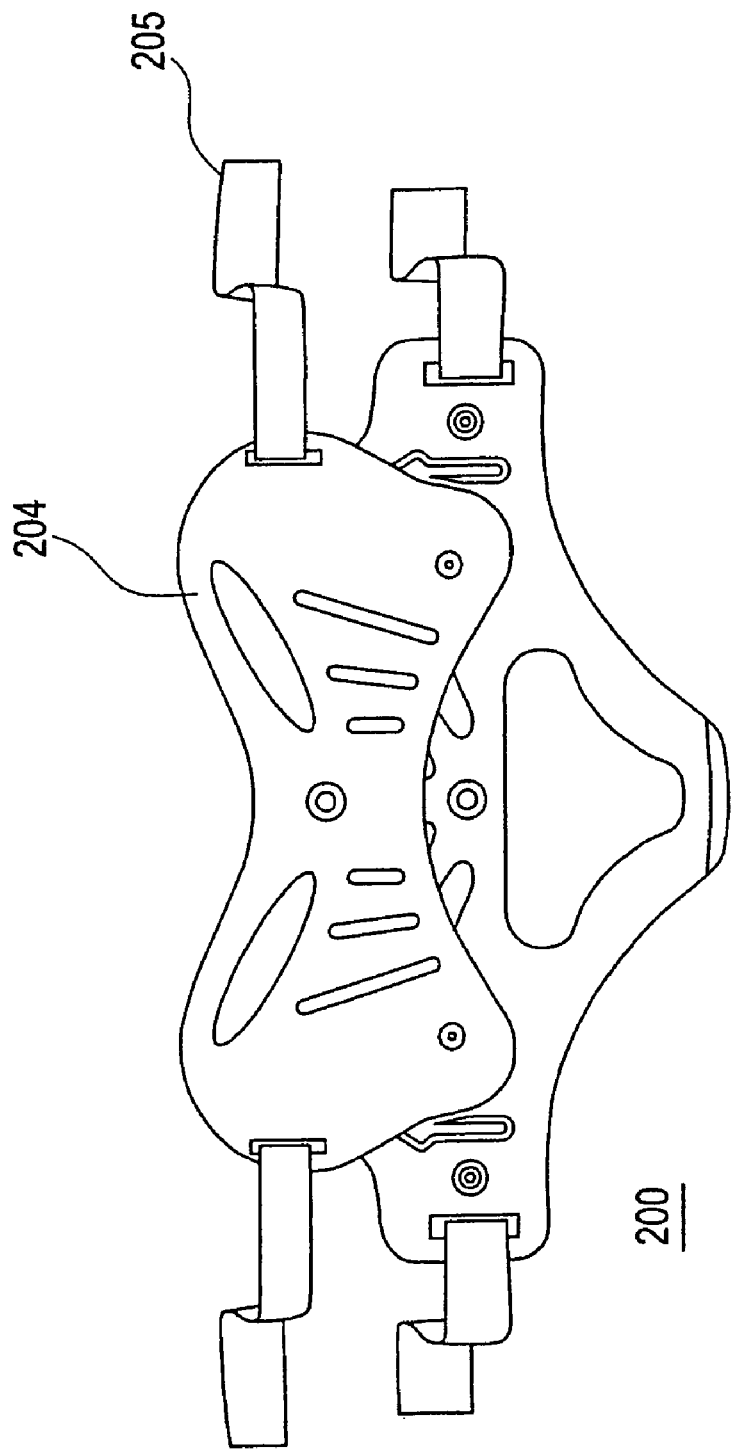
FIG. 1B is a plan view of the rear portion of a cervical collar according to an illustrative embodiment of the invention.

Referring now to FIG. 1A and FIG. 1B, there is shown a view of the elements that comprise an overall preferred assembly of a cervical collar made in accordance with an embodiment of the present invention. A padded cervical collar 110 is supported by an anterior assembly 100, which is comprised of a chin strut 102 and an anterior plate assembly 104. The anterior plate assembly 104 is itself preferably comprised of two pieces: an upper front plate 106 and a lower front plate 108. A posterior assembly 200 is similarly comprised of an occipital support 204 and a molded back plate 300. Finally, a detachable rear strut 202 and/or a head strap 205 is provided in certain embodiments. The rear strut would not be engaged when the benefit of a freely moving back portion is desired. Occipital support 204 and head strap 205 have been omitted from posterior assembly 200 in FIG. 1A so that strut 202 may be seen more easily. When assembled and worn, these elements provide a collar that supports the cervical spine exceptionally well. It is noted that the front and rear portions of the brace may be in the form of a "vest" wherein the front vest portion is preferably of a rigid material and is rigidly attached to the cervical collar, and the back vest portion may be a rigid assembly or flexible assembly or merely straps to secure the front vest portion around the wearer. The back vest portion may be capable of being rigidly or flexibly attached to the cervical collar, however in the preferred embodiment it moves freely with respect to the collar.

As will be further appreciated by those familiar with such devices, the design of the anterior assembly of the present invention is also well-suited to support and accommodate injuries to the cervical thoracic junction, that is, injuries to the region of the lower cervical spine and the upper thoracic spine, while the design of the posterior assembly, in particular with a head strap 205 provides support for patients with upper cervical spinal injury. Further details of the anterior assembly are illustrated in FIGS. 2-6.

Figure 3B:
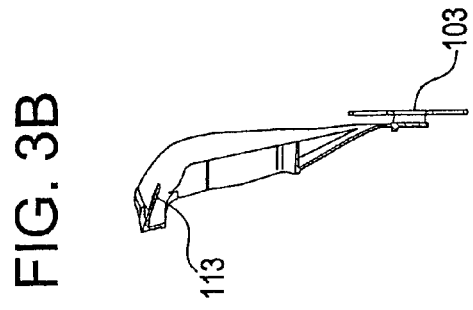
FIGS. 3A-3E are a set of orthographic views of a chin strut made in accordance with an illustrative embodiment of the invention.
Figure 3E:
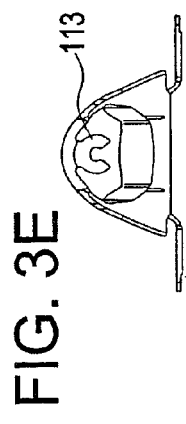
Figure 3A:
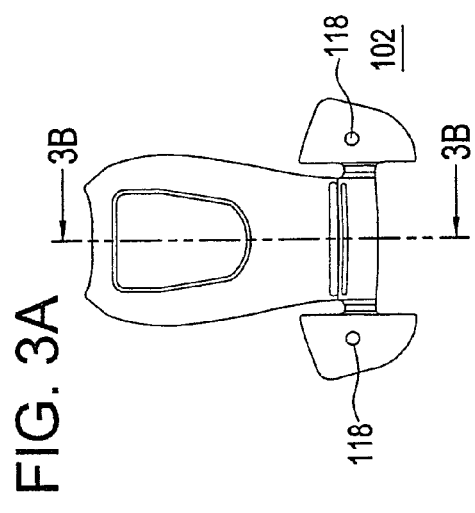
Figure 3C:
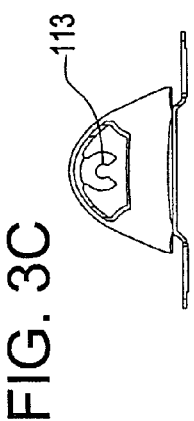
Figure 3D:
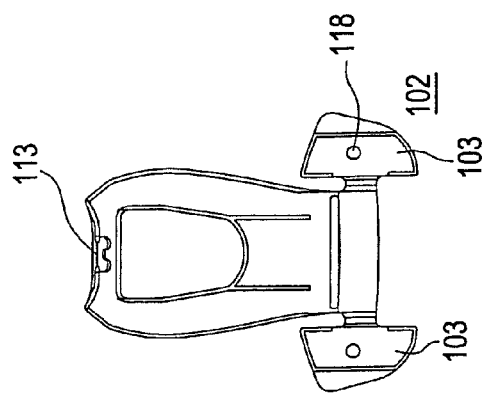
Figure 4:
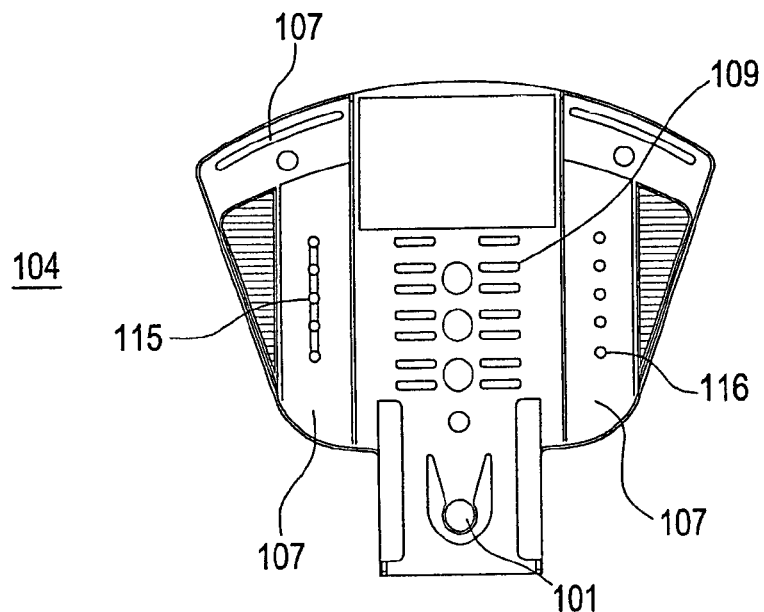
FIG. 4 is a plan view of the illustrative embodiment of an upper anterior front plate seen in FIG. 2.

As seen in FIG. 2, the chin strut 102 is most preferably provided with an adjustable affixation section 103, which most preferably is a hook-and-loop type fastener, although other types of fasteners or structures may be provided. Additional details of the chin strut 102 can be appreciated through review of FIGS. 3A-3D. FIG. 3A is a plan view of a chin strut and FIG. 3B is a cross-sectional elevation view taken at line B-B in FIG. 3A, and illustrates the adjustable affixation section 103 that is preferably disposed on a relatively flat and relatively flexible surface so that it may adjustably cooperate with the upper front plate 106 shown in FIG. 4. The chin strut 102 is preferably a contoured molded structure that extends upward toward the chin and includes an attachment point 113 that cooperates with the cervical collar 110. In a preferred embodiment, the attachment point 113 is designed to cooperate with existing elements of the cervical collar 110 so that no separate fastener is needed to affix these two subassemblies. Chin strut 102 is preferably attached to a cervical collar chin support 112, as shown in FIG. 1A. In this manner, the cervical collar 110 is attached to the anterior assembly in a manner that limits the movement of the chin upward and downward, as well as sideways and rotationally, and thereby stabilizes the wearer since the chin strut 102 is designed to have sufficient rigidity and stiffness to provide such stability. In accordance with the present invention, the chin strut 102 preferably supports the chin of the wearer and transfers force from this point directly to the sternum, rather than the chin of the wearer being supported only by the padded cervical collar 110. Chin strut 102 may be affixed to upper front plate 106 by hook and loop fasteners as herein above described, or by some other appropriate means. As an example, upper front plate 106 can include an elongated slot 115 as shown in FIG. 4, for receiving a rivet 120 in chin strut 102. For this purpose, chin strut 102 includes hole 118. In this manner, chin strut 102 can slide along elongated slot 115. Alternatively, upper front plate 106 may include a series of holes 116, whereby once the correct position for chin strut 102 is determined, plastic rivets can be used through holes 116 and 118 to secure upper front plate 106 to chin strut 102.

Figure 5:
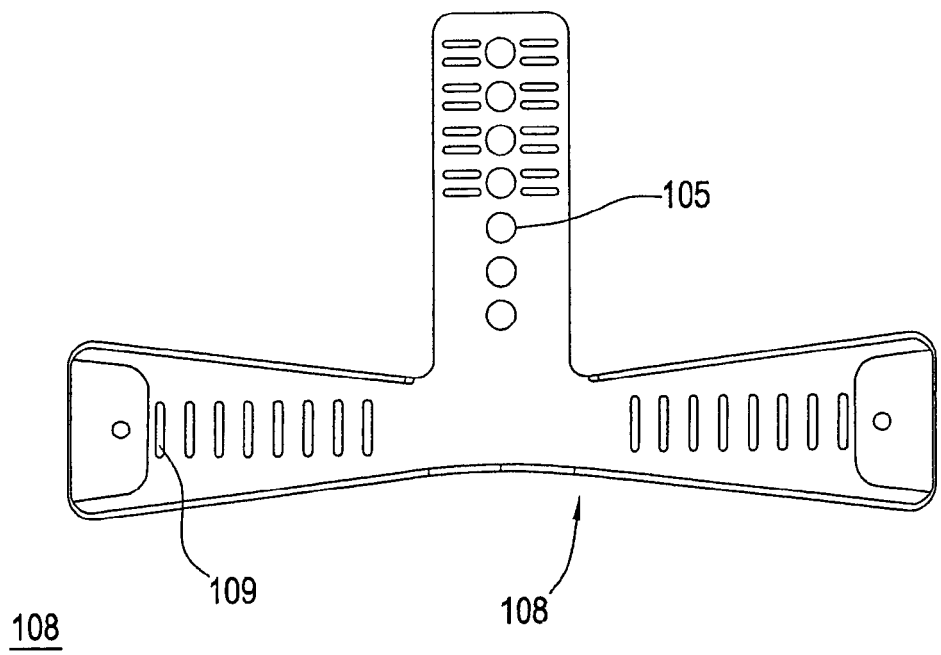
FIG. 5 is a plan view of the illustrative embodiment of the lower anterior front plate seen in FIG. 2.

Referring now to FIGS. 4-5, plan views of the upper front plate 106 and lower front plate 108 that preferably make up the anterior plate assembly 104 are shown. As seen in FIG. 4, the upper front plate 106 preferably includes affixation sections 107 that are designed to cooperate with the affixation section 103 described above with reference to the chin strut 102. If, as described with reference to the chin strut, a hook-and-loop fastener is employed, the affixation sections 107 would be designed and placed to be in a corresponding relationship with the affixation sections 103 when the chin strut 102 and the upper front plate 106 are brought together in an assembly and would include complementary hook-and-loop fasteners. Numerous other types of fasteners could be used, either integrally molded or formed as part of these components, or provided as separate pieces, so long as the upper front plate 106 or other corresponding structure could be removably and adjustably attached to the chin strut 102 to affect the stabilization function described above.

FIGS. 4 and 5 also illustrate a series of affixation points 105 that are used in to affix these two elements in a pre-determined relationship that is selected based upon the size of the wearer, the orientation of the head and neck, and other criterion familiar to those who use and apply cervical collars and cervical thoracic orthoses. An additional affixation point 101 (seen in FIG. 4) is preferably provided so that the anterior plate assembly 104 of the upper front plate 106 and the lower front plate 108 is adjustably secured after assembly, this particular affixation point 101 is also used to affix the chin strut 102 to the overall anterior assembly 100, as explained in further detail below. The upper and lower anterior plates 106, 108 also include slots 109 for attaching securing straps, which are illustrated in FIG. 1A. Both the upper and lower front plates 106, 108 also preferably molded from or die cut from a sheet of relatively flexible and strong plastic material, although any suitable material known to those in the art may be utilized. Although not illustrated, it is further understood by those of skill in the art that the components discussed with reference to FIGS. 4 and 5 can include padding or surfacing materials for patient comfort, or other purposes.

Figure 6:
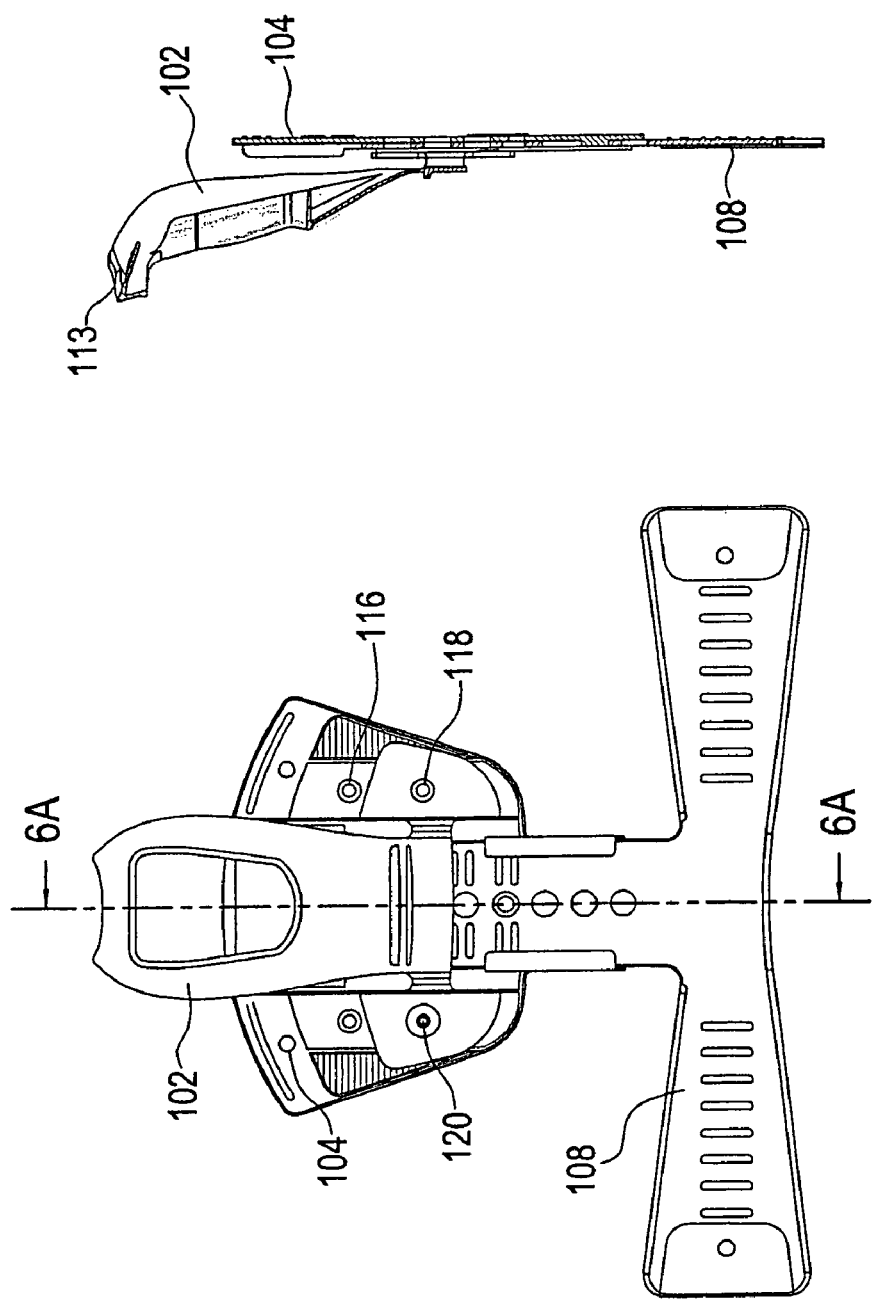
FIG. 6 is an illustrative embodiment of an anterior assembly including a chin strut.

The subassembly described above with reference to FIGS. 1-2 is further illustrated in FIGS. 6 and 6A where the arrangement of the components described with reference to FIGS. 3-5 is illustrated. As explained above, the adjustable affixation points 101, 105 are disposed so that upon assembly in proper alignment, the two portions can be adjusted and snapped or affixed together using any of a number of techniques and structures well known in the art. Lower front plate 108 is slidably engaged in upper front plate 106. Affixation point 101 is a button biased outwardly which locks into an affixation point 105 to secure lower front plate 108 to upper front plate 106. Upon completing this assembly process, the chin strut 102 is added to complete the anterior plate assembly 104. The preferred embodiment of the present invention illustrated permits the wearer or the person applying the cervical brace to the wearer to adjust the relative dimensions between the chin strut 102 and the placement of the anterior plate assembly at a comfortable and appropriate location on the thorax of the patient so that the force is adequately transferred and stability is maintained. Further adjustment of lower front plate 108 in upper front plate 106 is also facilitated to accommodate patients of different body types. As explained in further detail below, the anterior plate assembly 104 and the lower plate 108 are each adapted to receive straps or similar affixation elements that permit the entire cervical brace to be comfortably and securely fitted to the patient.

Figure 7:
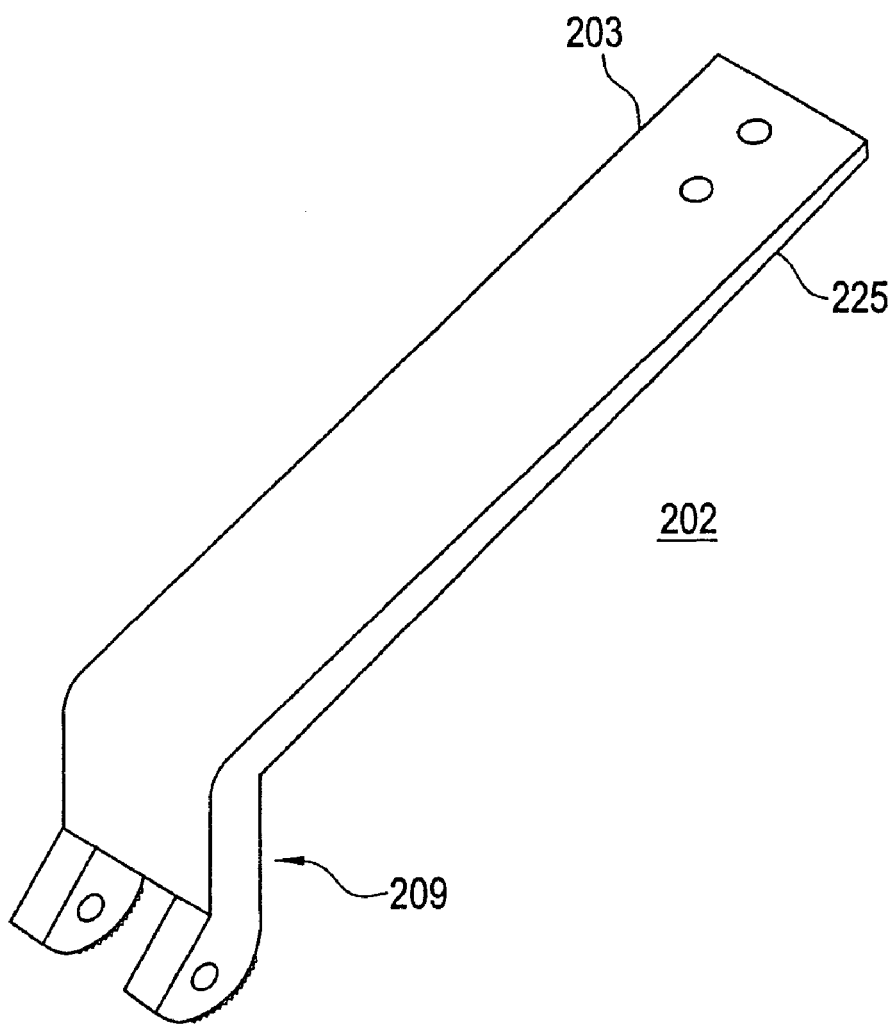
FIG. 7 is a perspective view of an illustrative embodiment of the invention depicting the posterior strut assembly seen in FIG. 1A.

Referring back to FIG. 1A, it was mentioned that a removable rear strut 202 is provided to connect the occipital support 204 of cervical collar 110 to the rest of the brace. The one end of the rear strut 202 is connected to an occipital support 204 that may include a head strap 205 that is used in certain indications to provide additional support. Extending from this end of this sub-assembly is the rear strut 202. Rear strut 202, when used, connects directly to cervical collar 110, either at occipital support 204 or at another point on the rear of cervical collar 110. Further details of this aspect of the present invention are illustrated in FIG. 7 and as seen therein, in a preferred embodiment, the rear strut 202 is preferably a carefully engineered component that has a distal end 203 that cooperates with posterior assembly 200 that is most preferably adjustable via a mechanism such as a screw adjustment wheel. A further feature of a preferred embodiment is the incorporation of a defined flexure point 225 at the point at which the rear strut 202 joins the posterior assembly 200. The proximal end 209 of the rear strut 202 is preferably constructed to permit rotation about a pivot point in a releasable fashion, as explained further below.

Figure 8:
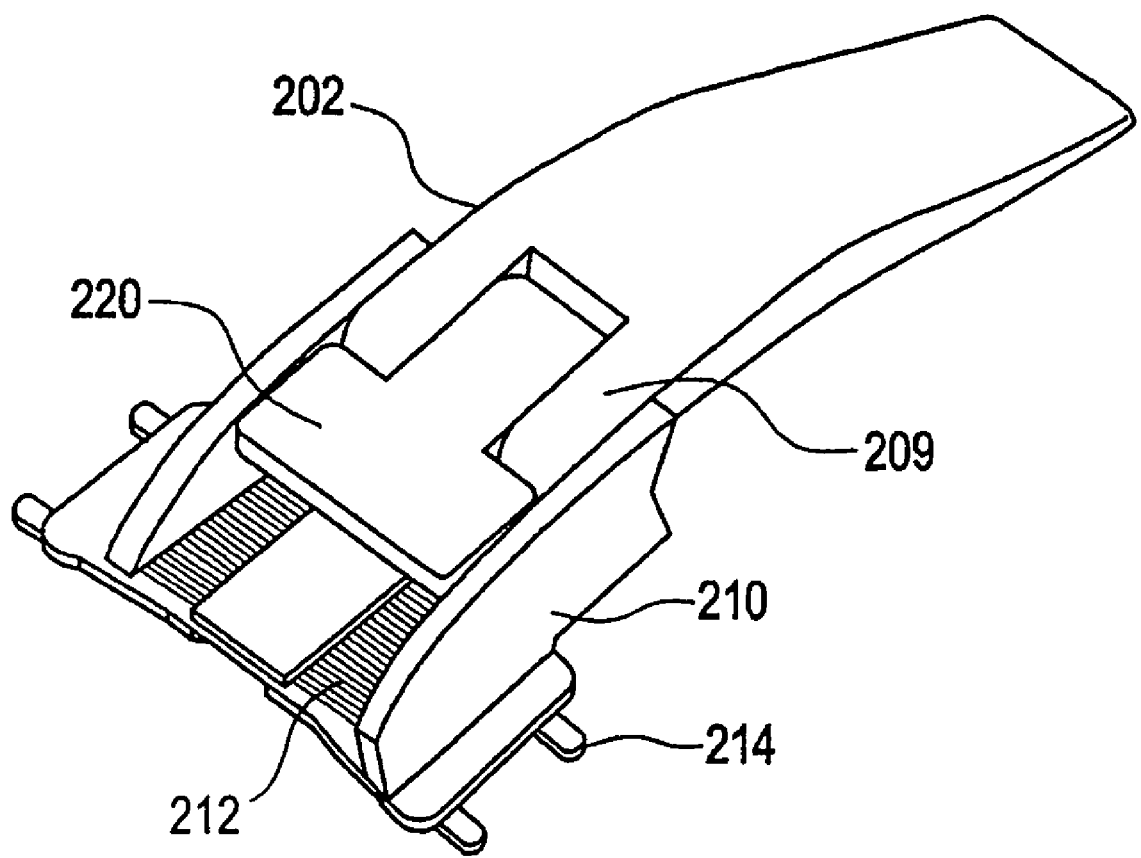
FIG. 8 is a perspective view, of a latch according to an illustrative embodiment of the invention.

Further details of the proximal end 209 of the rear strut 202 are illustrated in FIG. 8. As mentioned above, the rear strut 202 is permitted to rotate and, in a most preferred embodiment is also permitted to move vertically. As seen in FIG. 8 the proximal end 209 of the rear strut 202 cooperates with a rear struts housing 210, and is held in place by the operation of a rear strut latch 220, the details of which are explained below. The rear strut housing 210 preferably includes extensions 214 or other cooperation elements that permit it to be easily attached to the molded back plate 300, which is shown in FIG. 1A and the further details of which are described below.

Figure 9:
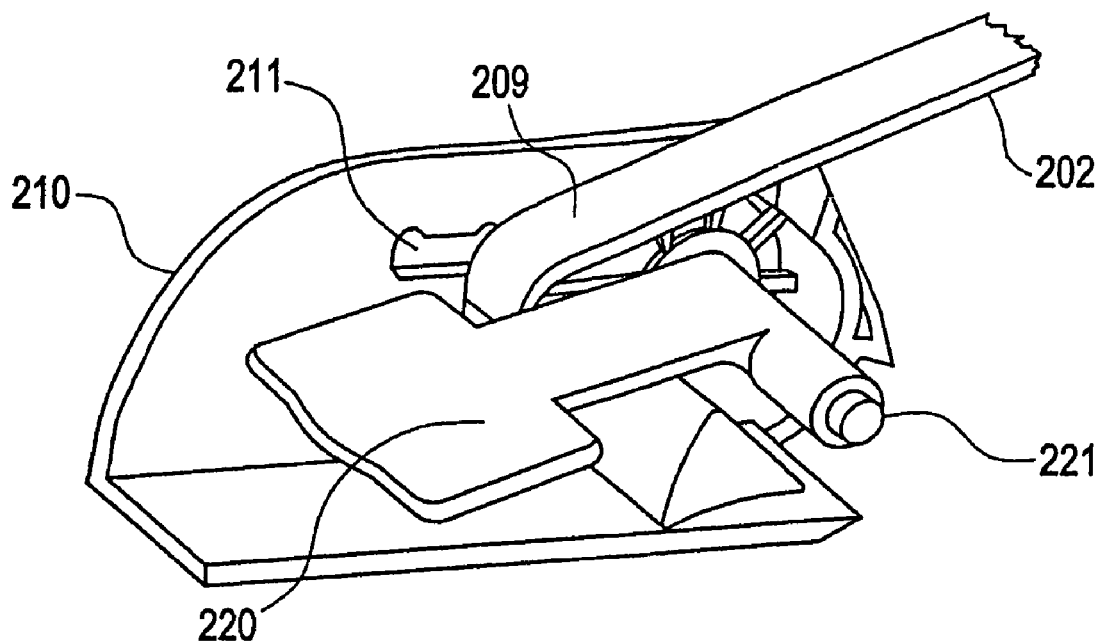
FIGS. 9-10 are two perspective views, partially cut away, of the latch shown in FIG. 8, illustrating respectively the locked and unlocked positions.
Figure 10:
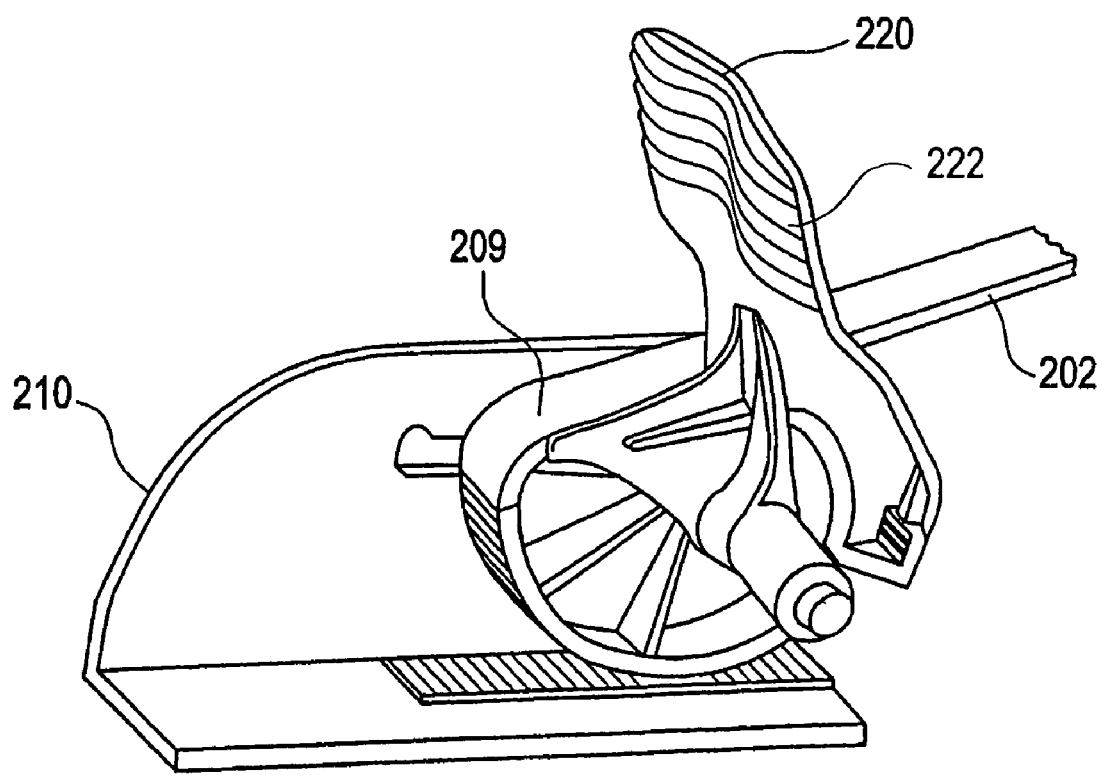

The construction and operation of the rear strut latch 220 is illustrated in FIGS. 9-10, which for the sake of clarity show a preferred embodiment of the present invention in which a portion of one side of the rear strut housing 210 has been cut away. Referring to FIG. 9, the cooperation of the rear strut housing 210 and the proximal end 209 of the rear strut 202 with the rear strut latch 220 can be appreciated. The rear strut latch 220 defines an axis of rotation 221 which cooperates with a receiving slot 211 that has a plurality of detents that together define a position for the axis of rotation 221 relative to the housing 210. It is due to the provision of this elongated receiving slot that the rear strut 202 may move relative to the point at which the rear strut housing is attached to the patient, and in this manner effect adjustability relative to the patient's head and rotational position of the head relative to the neck. The rear strut 202 is held firmly in place by the eccentric offset of the axis of rotation 221 so that when the rear strut latch 220 is raised, as shown in FIG. 10, the rear strut 202 is slightly elevated and free to move within the constraint provided by the engagement of ends of the axis of rotation 221 with the receiving slot 211. To further enhance the fixed position of the rear strut 202 when the rear strut latch 220 is closed or in the locked position, serrations 212 are provided, as are corresponding knurled surfaces 222 in the proximal end 209 of the rear strut 202. Although interlocking engagement between two sets of ridges, knurls or similar structures represents a preferred embodiment, those of skill in the art will appreciate that there are a number of other structures and techniques for obtaining a similarly secure locking engagement that can be freely substituted in this type of latching mechanism.

Figure 11:
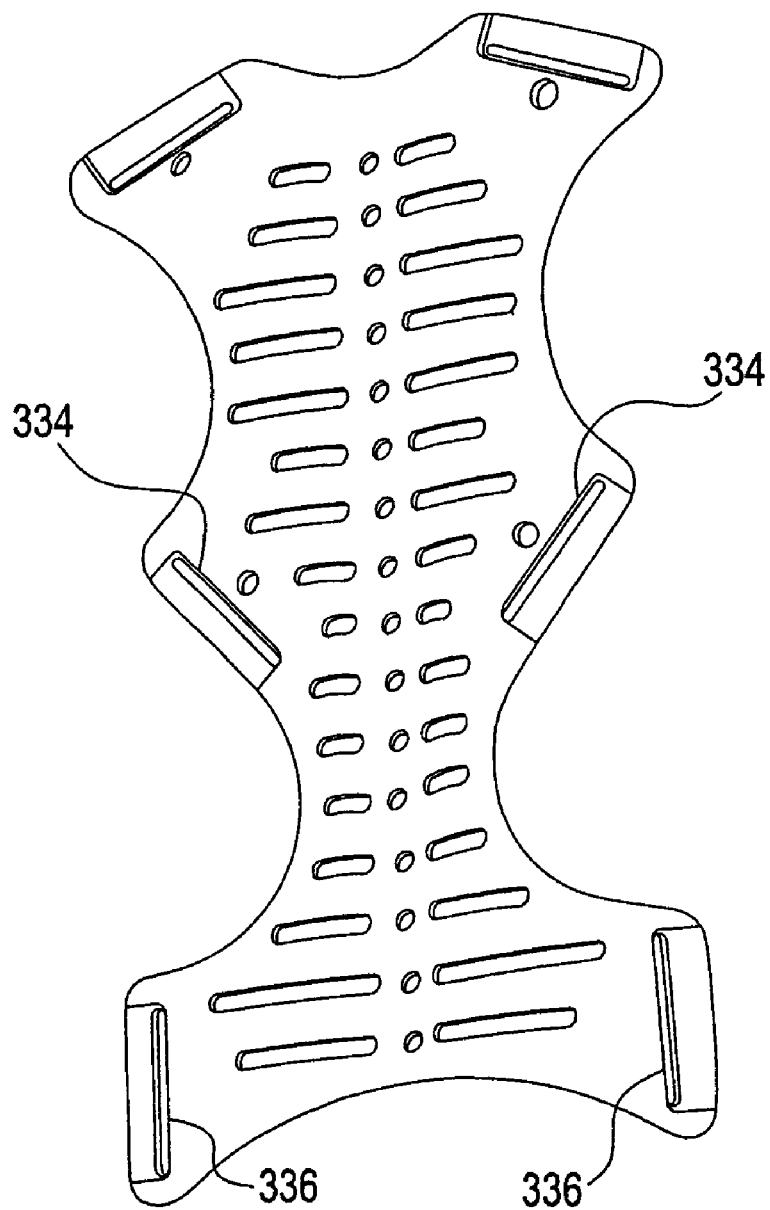
FIG. 11 is a molded back plate according to an illustrative embodiment of the invention.

Referring to FIGS. 1A and 11, a molded back plate 300 is also part of a preferred embodiment of the present invention. The back plate may be rigid or conformable so as to flex with the back. A conformable back may include rigid and nonrigid portions. As explained above, the molded back plate 300 is comprised of a molded section 310 and a plurality of straps 320,330 for affixing the cervical collar assembly to the wearer. Upper straps 320 are disposed so that they engage co-operating latches or buckles 322 that are attached to the anterior assembly 100. Lower straps 330 surround the thorax and engage co-operating latches or buckles 332 that are also attached to the anterior assembly 100, and most preferably attached to the lower plate 108. Both upper straps 320 and lower straps 330 are adjustable. The manner of adjustability of straps 330 is important to the proper fitting of the cervical brace of the present invention as well as to the comfort of the wearer. In a preferred embodiment, straps 330 are attached to molded back plate 300 at slots 334. Each strap 330 then passes through a buckle 332, and back to molded back plate 300 at slots 336. Strap 330 can then be attached to lower back plate 300 in any conventionally adjustable manner, such as by adjustable buckles. Strap 330 may also pass through slot 336 and then the end of strap 330 can be secured to another portion of strap 330 using hook and loop fasteners A further feature of the present invention is also visible with reference to FIG. 1A, namely the cooperation between the posterior assembly 200 and the molded back plate 300. As described above with reference to FIG. 8, the rear strut housing 210 preferably includes extensions 214 or other cooperating elements that permit it to be easily attached and detached to the molded back plate 300. As illustrated in FIG. 1A, the molded back plate 300 also preferably includes receiving slots 311 that are adapted to accept and engage the extensions 214 of the rear strut housing 210 so that the posterior assembly 200 and the molded back plate 300 are locked together as the cervical brace of the present invention is fitted to the patient. As mentioned with reference to other aspects of the present invention, although the extensions 214 and receiving slots 311 represent a preferred embodiment of the present invention, other structures can be readily substituted.

Thus, it will be appreciated that upon assembly of the above-described components, a cervical brace is produced capable of securely and comfortably supporting a patient suffering from any of a variety of cervical and cervico-thoracic injuries. One particular advantage of the design described herein is that is can be used in a modular manner; in other words, certain of the components described herein can be deleted from the overall assembly to create a specialized brace. For example, some patients may not need the head strap 205 described above. Similarly some patients may be adequately supported by an assembly that does not include the rear strut 202. Therefore, rear strut 202 may be used without head strap 205, and head strap 205 may be used without rear strut 202.

While the invention has been described by illustrative embodiments, additional advantages and modifications will occur to those skilled in the art. Therefore, the invention in its broader aspects is not limited to specific details shown and described herein. Modifications may be made without departing from the spirit and scope of the invention. Accordingly, it is intended that the invention not be limited to the specific illustrative embodiments, but be interpreted within the full spirit and scope of the appended claims and their equivalents.

The invention claimed is:

1. A cervical brace comprising:
    a cervical collar having a front collar portion and a rear collar portion, wherein the rear collar portion comprises an occipital support and wherein the collar extends to at least the shoulder level of a user;
    a vest comprising a front vest portion and a back vest portion, and attachment mechanism to attach the front vest portion to the front collar portion to limit movement of the front vest portion with respect to the cervical collar; and
    the back vest comprising a rigid plate;
    wherein the back vest portion is free to move with respect to the cervical collar rear portion while the back vest portion otherwise remains an attached part of the cervical brace, attached other than at the cervical collar and the back vest portion remains in place with respect to the user thereby providing back support.

2. The cervical brace of claim 1 wherein the front vest portion comprises an upper front plate and a lower front plate wherein the upper front plate is adjustably attached to the lower front plate to accommodate wearers of different sizes and phenotypes.

3. The cervical brace of claim 1 further comprising an attachment mechanism for attaching a rear strut to the back vest portion and the rear collar portion.

4. The cervical brace of claim 1 further comprising one or more straps to attach the rear vest portion to the front vest portion.

5. The cervical brace of claim 1 wherein the back vest portion is a conformable plate.

6. A method of bracing the cervical spine or thoracic spine of a patient comprising:
    attaching a cervical collar to the patient wherein the cervical collar has a front collar portion and a rear collar portion with an occipital support and wherein the collar extends to at least the shoulder level of a user;
    attaching a vest to the patient wherein the vest has a front vest portion and a back vest portion, the back vest comprising a rigid plate;
    attaching the front vest portion to the front collar portion; and
    providing the back vest portion free from attachment to the rear collar portion while the back vest portion otherwise remains an attached part of the cervical brace, attached other than at the cervical collar and the back vest portion remains in place with respect to the user thereby providing back support.

7. The method of claim 6 further comprising securing the back vest portion to the front vest portion with one or more straps.

8. The method of claim 7 wherein the front vest portion comprises an upper front plate and a lower front plate wherein the upper front plate is adjustably attached to the lower front plate, the method further comprising:
    adjusting the lower front plate with respect to the upper front plate to accommodate wearers of different sizes and phenotypes.

9. A cervical brace comprising:
    a cervical collar having a front collar portion and a rear collar portion, wherein the rear collar portion comprises an occipital support and the front collar portion comprises a chin support, and wherein the collar extends to at least the shoulder level of a user;
    a vest comprising a front vest portion having an area disposed over the sternum of a wearer and a back vest portion;
    a chin strut extending from the sternum area of the front vest portion to the chin support to limit movement of the front vest portion with respect to the cervical collar, the chin strut detachably connected to the chin support; and
    wherein the back vest portion is free to move with respect to the cervical collar rear portion while the back vest portion otherwise remains an attached part of the cervical brace, attached other than at the cervical collar and the back vest portion remains in place with respect to the user thereby providing back support.

10. A method of bracing the cervical spine or thoracic spine of a patient comprising:
    attaching a cervical collar to the patient wherein the cervical collar has a front collar portion and a rear collar portion with an occipital support and wherein the collar extends to at least the shoulder level of the patient;
    attaching a vest to the patient wherein the vest has a front vest portion and a back vest portion;
    attaching the front vest portion to the front collar portion with a chin strut extended from an area of the front vest portion disposed over a wearer's sternum to a chin support on the front collar portion, wherein the chin strut is detachable; and
    providing the back vest portion free from attachment to the rear collar portion while the back vest portion otherwise remains an attached part of the cervical brace, attached other than at the cervical collar and the back vest portion remains in place with respect to the user thereby providing back support.

11. A cervical brace comprising:
a cervical collar having a front collar portion and a rear collar portion, wherein the rear collar portion comprises an occipital support and wherein the collar extends to at least the shoulder level of a user;
a vest comprising a front vest portion and a back vest portion, and attachment mechanism to attach the front vest portion to the front collar portion to limit movement of the front vest portion with respect to the cervical collar;
the cervical collar having a chin support and the front vest portion having an area disposed over the sternum of the wearer, wherein the attachment mechanism to attach the front vest portion to the front collar portion comprises a chin strut extends from the sternum area of the front vest portion to the chin support;
the back vest comprising a rigid plate; and
wherein the back vest portion is free to move with respect to the cervical collar rear portion while the back vest portion otherwise remains an attached part of the cervical brace, attached other than at the cervical collar and the back vest portion remains in place with respect to the user thereby providing back support.

12. The cervical brace of claim 11 wherein the chin strut is detachably connected to the chin support.

13. The cervical brace of claim 11 wherein the chin strut is adjustably attached to the front vest portion.

14. The cervical collar of claim 13 wherein adjustability is provided by attachment of the chin support and the front vest portion using hook-and-loop fasteners.

15. The cervical brace of claim 11 wherein the chin strut extends in a straight line from the sternum area of the front vest portion to the chin support.

16. A method of bracing the cervical spine or thoracic spine of a user comprising:
attaching a cervical collar to the patient wherein the cervical collar has a front collar portion and a rear collar portion with an occipital support and wherein the collar extends to at least the shoulder level of the user;
attaching a vest to the user wherein the vest has a front vest portion and a back vest portion, the back vest comprising a rigid plate;
providing a chin strut extending from an area of the front vest portion disposed over the user+s sternum to a chin support on the front collar portion; and
providing the back vest portion free from attachment to the rear collar portion while the back vest portion otherwise remains an attached part of the cervical brace, attached other than at the cervical collar and the back vest portion remains in place with respect to the user thereby providing back support.

17. The method claim 11 wherein the chin strut provided is detachable.

18. The method of claim 16 wherein the chin strut is adjustably attached to the front vest portion, the method further comprising:
adjusting the chin strut with respect to the front vest portion.

19. The method of claim 16 comprising extending the chin strut in a straight line from the sternum area of the front vest portion to the chin support.

20. The method of claim 16 further comprising:
adjusting the vertical height of the front vest portion independently of the adjustment of the relative position of the chin strut and the front vest portion.

* * * * *